United States Patent [19]
Kratzer

[11] Patent Number: 5,213,577
[45] Date of Patent: May 25, 1993

[54] DEVICE FOR EXAMINING THE FUNCTIONS OF THE ENDOTHELIUM OR THE INTIMA OF BLOOD VESSELS

[76] Inventor: Michael Kratzer, Leopoldstrasse 56, 8000 Munich 40, Fed. Rep. of Germany

[21] Appl. No.: 629,811

[22] Filed: Dec. 21, 1990

[51] Int. Cl.$^5$ .............................................. A61M 25/00
[52] U.S. Cl. ...................................... 604/101; 604/96; 606/191; 606/192; 606/194
[58] Field of Search ................................. 604/96–101; 606/191–194

[56] References Cited

U.S. PATENT DOCUMENTS

| | | | |
|---|---|---|---|
| 2,642,874 | 6/1953 | Keeling | 604/101 |
| 2,849,002 | 8/1958 | Oddo | 604/101 |
| 3,411,506 | 11/1968 | Velasco | 604/101 |
| 4,423,725 | 1/1984 | Baran et al. | 604/101 |
| 4,610,662 | 9/1986 | Weikl et al. | 604/53 |
| 4,696,668 | 9/1987 | Wilcox | 604/28 |
| 4,983,167 | 1/1991 | Sahota | 606/194 |
| 5,087,247 | 2/1992 | Horn et al. | 604/98 |
| 5,090,958 | 2/1992 | Sahota | 606/192 |

*Primary Examiner*—Robert A. Hafer
*Assistant Examiner*—Kerry Owens
*Attorney, Agent, or Firm*—Anthony A. O'Brien

[57] ABSTRACT

The invention relates to a device for examining the functions of the endothelium or the intima of blood vessels. A tube (1) has at least one outlet (6) and at least one inlet (7) spaced along the wall thereof. Outlet (6) communicates with a connector (8), inlet (7) communicates with another connector (9). Connectors (8, 9) are provided in tube (1) at the end thereof projecting from blood vessel (4).

17 Claims, 2 Drawing Sheets

DEVICE FOR EXAMINING THE FUNCTIONS OF THE ENDOTHELIUM OR THE INTIMA OF BLOOD VESSELS

The invention relates to a device for examining the functions of the endothelium or the intima of blood vessels.

There has not been available so far a practicable method of examining the functions of the endothelium or the intima of blood vessels in vivo on humans or animals.

Accordingly, the object of the invention is to provide a device for examining the functions of the endothelium or the intima of blood vessels by means of which healthy physiological endothelium or intima cells may be examined.

The essential advantage of the inventive device is that it enables direct in vivo examinations to be performed on healthy endothelial or intimal cells of humans and animals.

Advantageously, the examinations made using the inventive device will yield information on important endothelial and intimal functions. This will provide insights into the interaction of the endothelium with the coagulation system, i.e. also for instance on thrombosis or hemorrhage tendencies or on early arteriosclerotic changes.

Preferably, the inventive device may be used to perform tests of animals as often as desired and in a manner which inflicts no pain or harm on the animal.

Using the invention, valuable knowledge may be gained which has importance for the development of medicaments to be used e.g. in the treatment of arteriosclerosis.

Advantageous further developments of the invention are specified in the dependent claims.

The invention and embodiments thereof will now be explained in greater detail under reference to the drawings.

The invention resulted from the following considerations. To enable in vivo examinations of the endothelial or intimal cells of the blood vessels of humans and animals to be conducted, access to the endothelial or intimal cells lining the blood vessels is required. For this reason, an assembly was created which is adapted to be introduced in a vessel such as a vein or an artery in the manner of a catheter. At a predetermined location of the vessel, a section thereof is then sealed at both ends. A solution is introduced in the sealed section and perfused to contact the endothelial or intimal cells lining the vessel within that section. Subsequently, the solution is withdrawn from the section and examined. Changes the solution has undergone may then be detected by comparative measurements. These changes allow conclusions to be drawn as to the function of the endothelial or intimal cells.

Figure 1:
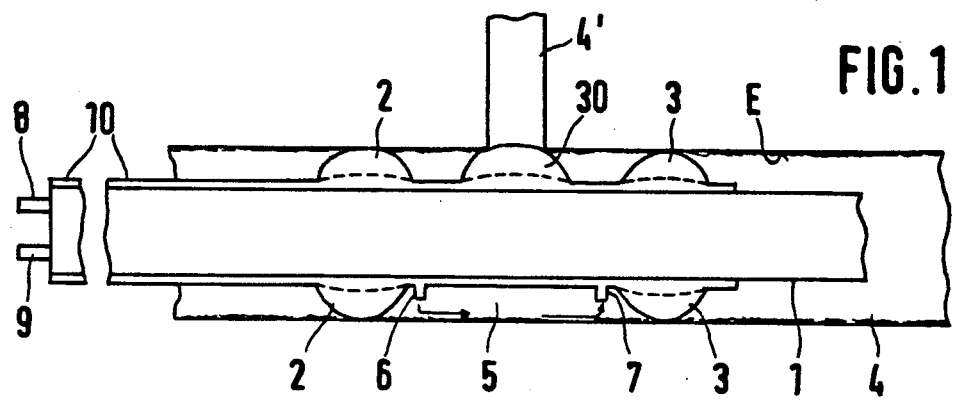
FIG. 1 shows a schematic view of a device in accordance with the invention for explaining the fundamental operation thereof.

According to FIG. 1, one embodiment of the present invention comprises a tube 1 having spaced means 2, 3 thereon which can be actuated after tube 1 has been introduced in a blood vessel 4 in such a manner that they form a seal between the periphery of tube 1 and the inner walls of blood vessel 4. This results in the creation between means 2 and 3 of an area 5 which is isolated from the remainder of the blood vessel. Endothelium E or the intima covers the inner walls of blood vessel 4. The present device also has between means 2, 3 at least one outlet 6 and at least one inlet 7 allowing a solvent to be introduced into area 5 through outlet 6 and to be withdrawn through inlet 7. Preferably, outlet 6 is provided in the vicinity of one said means 2 while inlet 7 lies in the vicinity of the other means 3. Outlet 6 and inlet 7 may have the form of short tubular members extending through the walls of tube 1 or of simple openings in the walls of tube 1. The solvent introduced through outlet 6 flows through area 5 from one end thereof to the other. By providing a plurality of outlets 6 and a plurality of inlets 7 suitably uniformly spaced along the periphery of tube 1, a uniform superfusion of the endothelium or of the intima with the solvent may be effected within area 5.

The free end of the device has a connector 8 for introducing the solvent which communicates with outlet 6; it also has a connector 9 for withdrawing the solvent which communicates with inlet 7.

The aforesaid means 2, 3 preferably comprise annular balloonlike elements of the type known in another context, namely, the Grünzig heart catheter. More specifically, a plastic tube 10 concentrically surrounds tube 1. As the aforesaid means, plastic tube 10 has zones 2, 3 which are more flexible than the remainder of the plastic tube. The space between tube 1 and plastic tube 10 is filled with a—preferably liquid—medium. In the normal condition, zones 2, 3 correspond to the dashed outlines. Once the aforesaid medium is pressurized, flexible zones 2, 3 flex outwardly so as to engage blood vessels 4, each providing a seal between the device and blood vessel 4. In case outlet 6 and inlet 7 are formed by short lengths of tubing or stubs, they are introduced through sealed openings in plastic tube 10. If outlet 6 and inlet 7 are formed by openings in the wall of tube 1, these openings are located behind sealed openings in plastic tube 10.

Figure 2:
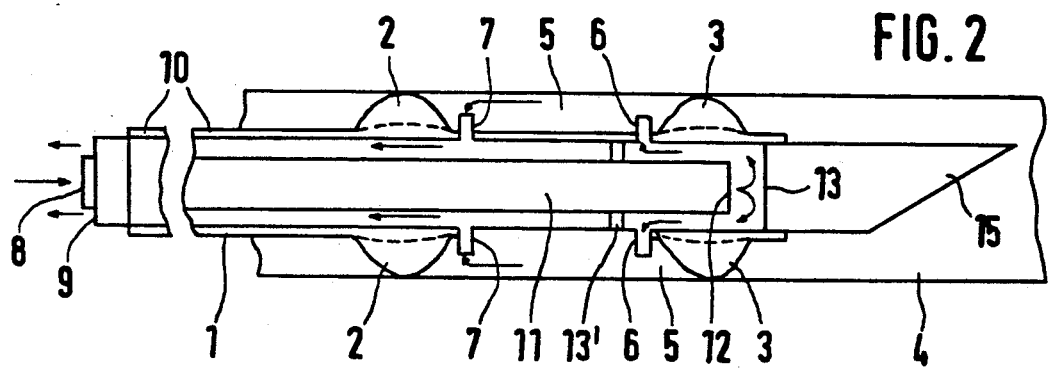
FIGS. 2 to 6 show embodiments of the inventive device.

FIG. 2 shows an inventive device wherein communication between connector 8 and outlet 6 is provided by an inner tube 11 of which the open end 12 is disposed in front of the closed end 13 of tube 1 so that the incoming solvent flows from open end 12 to outlet 6, which again has the form of an opening in the wall of tube 1 or of a stub member sealingly extending through the wall of tube 1. Inlet 7 also has the form of an opening in the wall of tube 1 or of a stub member extending through the wall of tube 1. The solvent flows through inlet 7 from area 5 to the space between inner tube 11 and tube 1. To prevent the solvent flowing through outlet 6 from mixing with the solvent flowing through inlet 7, a partition 13' is provided to seal the space between tube 1 and inner tube 11. Partition 13' is located below area 5 between inlet 6 and outlet 7, preferably in the vicinity of inlet 6.

Figure 3:
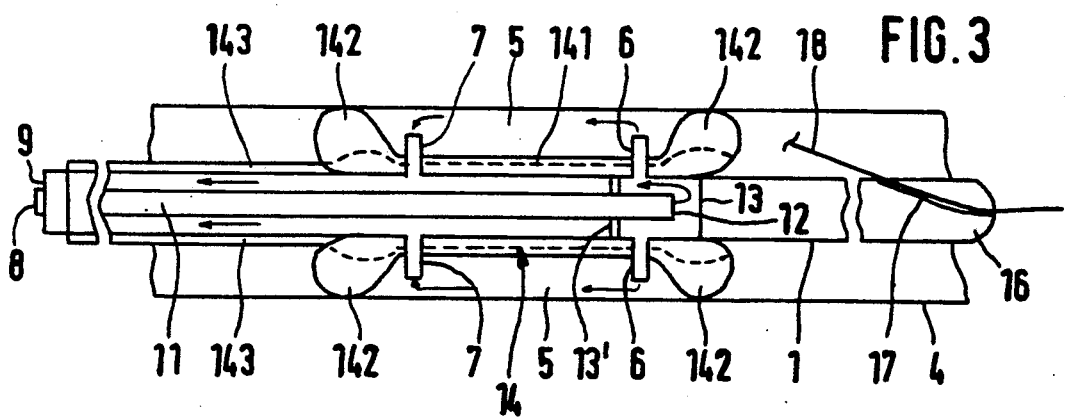

FIG. 3 shows an embodiment in which means 2, 3 comprise an inflatable cuff-like member 14 which annularly surrounds tube 1 and has a relatively inflexible central portion 141 and relatively flexible end portions 142. Member 14 is in sealed communication with conduit 143 which may extend through tube 1, may surround tube 1 concentric or may comprise a tubing section externally attached to tube 1. If conduit 143 extends through tube 1, conduit 143 extends through the wall of tube 1 in sealed relationship therewith. The dashed lines show member 14 in the non-expanded condition. The medium to be pressurized, as previously mentioned under reference to FIG. 2, is used in the embodiment of FIG. 3 as well in the interior of member 14 and in conduit 143. Inlet 6 and outlet 7, which again may be simple openings in the wall of tube 1 or stub members, are disposed below sealed openings in central portion 141 or extend through such openings.

According to FIG. 2, the front end of tube 1 may have an end portion tapered to a point so as to facilitate the introduction thereof in a blood vessel 4.

According to FIG. 3, the end portion of tube 1 may have a head portion 16 thereon which is rounded at its free end so as to facilitate its advance in a blood vessel 4. Head portion 16 may have a passage 17 therethrough which extends from the free end thereof to one side of head portion 16. Preferably, one exit opening of passage 17 is centrally disposed on the free end. Passage 17 is provided to receive in a manner known per se a guide wire 18 for guiding the assembly as it is being introduced in a blood vessel 4.

Figure 4:
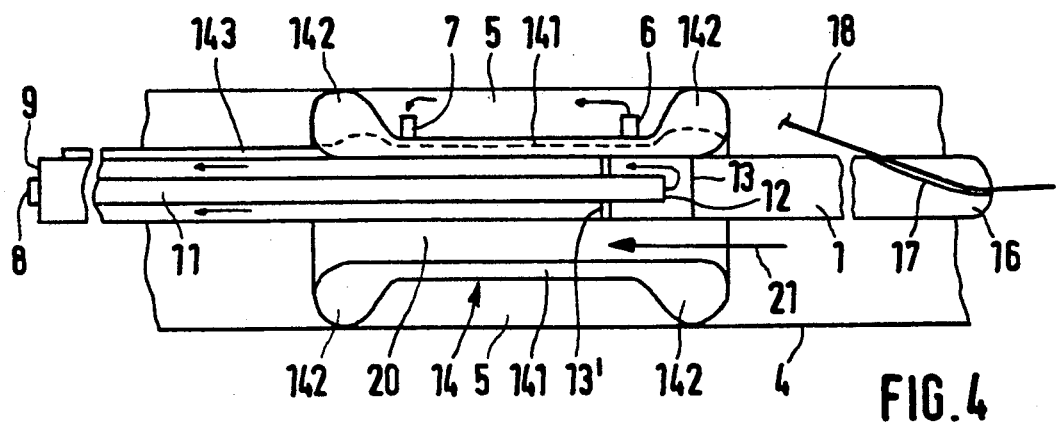

In the embodiment shown in FIG. 4, the annular cuff-like member has in its expanded condition an inner diameter greater than the outer diameter of tube 1. Tube 1 is secured to the inner wall of member 14. In the expanded condition, a space 20 is formed between tube 1 and member 14 through which blood may flow e.g. in the direction of arrow 21 when the assembly is located inside a blood vessel 4 such as an artery. What this means is that area 5 may be isolated from the inner walls of artery 4 without interrupting the flow of blood through the artery.

Generally, the previously mentioned flow of blood can be obtained in the embodiments shown in 1 to 3 by providing a by-pass between locations on opposite sides outside zones 2, 3 or of member 14. FIG. 1 shows an exemplary bypass line by dot-dashed line 23.

In all the embodiments shown above, it is contemplated to provide within area 5 another flexible zone 30 (FIG. 1) which does not extend annularly along the entire circumference, but only along a portion thereof. This zone 30 may be used to seal branchings along blood vessels 4' within area 5; branchings of this kind may interfere the tests to be conducted. It is contemplated also to select a length of zone 30 in the longitudinal direction of tube 1 such that zone 30 merges with zones 2 and 3 in that portion of the circumference.

Figure 5:
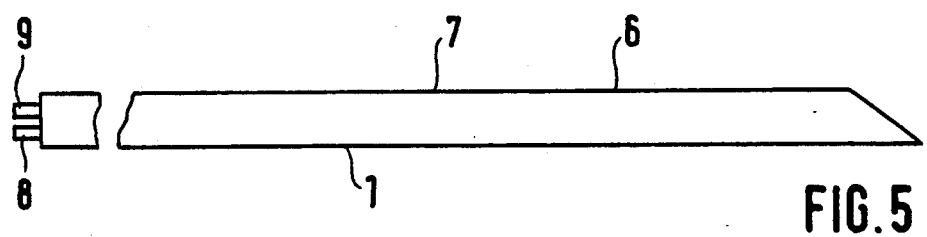

A particularly simple inventive device is shown in FIG. 5. Accordingly, that device consists merely of a tube 1 which has at least one inlet 6 and at least one outlet 7 disposed in a spaced relationship and conveniently formed by openings in the wall of tube 1. In this case, seals are effected externally by pinching blood vessel 4 externally of inlet and outlet 6, 7 by means such as blade-like compressing elements spaced along a carrier. Communication between connectors 8, 9 and inlet 6 and outlet 7 can be established by any means desired, e.g. as described in the context of FIGS. 2 and 3.

In the embodiments of FIGS. 1 to 5, tube 1 preferably consists of metal, inner tube 11 of metal or plastic, tube 10 (FIGS. 1 and 2) of plastic with portions having different flexibility properties, conduit 143 (FIGS. 3 and 4) of plastic and member 14 (FIGS. 3 and 4) of plastic with portions having different flexibility properties.

The part referred to as end 13 may be a transverse wall disposed in the end area or at any other location of tube 1 to seal the cavity of tube 1.

Figure 6:
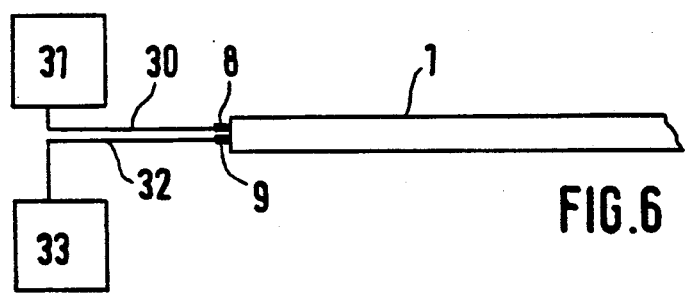

FIG. 6 shows that connector 8, through which the aforesaid solution is introduced, communicates through conduit 30 with a reservoir 31 holding a supply of that solution. Connector 9 communicates through another conduit 32 with analysis means 33. In operation, solution is withdrawn from reservoir 31 and introduced to area 5 through conduit 30 and connection 8 and the at least one outlet 6 communicating therewith. It is perfusingly contacted with the endothelial or initimal cells lining the blood vessel in area 5. The solution is passed on through inlet 7 to connector 9 and through conduit 32 to analysis means 33. The latter exmines the extent to which the solution supplied through connector 9 has been affected by having contacted the endothelial or intimal cells. To this end, analysis means 33 compares the solution supplied through conduit 32 with solution withdrawn from reservoir 31. Thus, the invention also teaches a system comprising a combination of reservoir 31, the catheter-like assembly and analysis means 33 and the aforesaid communications between connectors 8, 9 and conduit 30, 32.

Vasopressin analog (DDAVP) may be added to the inflowing solution to act on the endothelial cells so that these release Willebrand factor, which the analysis means then proceeds to measure.

I claim:

1. A device for examining a function of the endothelium or the intima of a blood vessel, comprising: a tube having in its wall at least one outlet and an inlet in spaced relationship to each other; first and second connectors; said outlet and said inlet communicating with said first and second connectors, respectively; said first and second connectors extending from an end of the tube projecting from the blood vessel; a reservoir communicating with the first connector for holding and discharging a solution through the first connector and the outlet into the blood vessel; and analysis means communicating with the second connector for receiving a solution from the blood vessel through the inlet and second connector; said analysis means detecting differences between the solution from the reservoir and the solution from the blood vessel to determine a function of the endothelium or the intima of the blood vessel.

2. A device as in claim 1, including seal means provided laterally adjacent said outlet and said inlet, respectively, and on opposite sides of an area defined by the outlet and the inlet; said seal means adapted to selectively provide a seal between the periphery of the tube and an inner wall of the blood vessel.

3. A device as in claim 2, wherein said seal means includes a plastic inflatable seal member concentrically surrounding the tube and having first and second spaced annular zones in which the material of the seal member is more flexible than the material in other areas of the seal member, so that said zones may flex outwardly in response to a medium inside the seal member being pressurized.

4. A device as in claim 3, wherein the seal member includes a third zone extending between the first and second zones along only one portion of the circumference of the seal member, said third zone consisting of said comparatively more flexible material than the other areas of the seal member.

5. A device as in claim 2, wherein said seal means includes an annular inflatable cuff-like plastic member placed over the tube and having a central portion and end portions, said end portions being comparatively more flexible than said central portion, and a conduit sealingly connected with the cuff-like plastic member in such a manner that a medium in the conduit and in the cuff-like plastic member when pressurized causes the end portions to flex outwardly to establish seals with the inner wall of the blood vessel.

6. A device as in claim 5, wherein said conduit concentrically surrounds tube.

7. A device as in claim 5, wherein said annular inflatable cuff-like plastic member has an inner diameter which is greater than the outer diameter of the tube when the medium is pressurized so as to form a passage for blood between the tube and the cuff-like plastic member.

8. A device as in claim 5, wherein said conduit extends inside the tube and sealingly extends through the wall of the tube.

9. A device as in claim 1, further comprising: a second tube disposed inside the first tube with one end of the second tube being located inside the first tube; a first partition in the first tube spaced from the one end of the second tube and sealing the lumen of the first tube; a second partition disposed—as seen from the first partition in the first tube—behind the one end of the second tube to seal the annular space between the second tube and the first tube said outlet communicating with the space between the first and second partitions; and said inlet being located in the area behind the second partition as seen from the first partition in the first tube.

10. A device as in claim 1, wherein the tube has an end portion tapered to a tip for introduction in a blood vessel.

11. A device as in claim 9, wherein the first tube has an end portion for extending into a blood vessel and which has a shape of a head portion rounded at its free end.

12. A device as in claim 11, wherein the head portion has a passage therein extending from the free end thereof to one side of the head portion, said passage being provided to receive a guide wire.

13. A device as in claim 1, wherein the tube has a plurality of outlets and a plurality of inlets distributed along circumferential areas of the tube.

14. A device as in claim 3, wherein said outlet and said inlet have the form of respective openings in the wall of the tube, said seal member having sealed openings in the area of the openings in the tube.

15. A device as in claim 3, wherein said outlet and said inlet each have the form of a short tubular stub extending through the wall of the tube, with the plastic seal member having sealed openings in the areas of said stubs.

16. A device as in claim 1, wherein the tube is metal.

17. A device as in claim 9, wherein said second tube consists of plastic or metal.

* * * * *